United States Patent
Migliaccio et al.

(10) Patent No.: US 9,962,355 B2
(45) Date of Patent: May 8, 2018

(54) MIXTURE OF FATTY ACIDS AND PALMITOYLETHANOLAMIDE FOR USE IN THE TREATMENT OF INFLAMMATORY AND ALLERGIC PATHOLOGIES

(71) Applicant: Raffaele Migliaccio, Monza (IT)

(72) Inventors: Raffaele Migliaccio, Monza (IT); Antonella Sardei, Molina di Malo (IT); Carmela Migliaccio, Monza (IT)

(73) Assignee: Raffaele Migliaccio, Monza (IT)

( * ) Notice: Subject to any disclaimer, the term of this patent is extended or adjusted under 35 U.S.C. 154(b) by 0 days. days.

(21) Appl. No.: 15/502,316

(22) PCT Filed: Aug. 3, 2015

(86) PCT No.: PCT/IB2015/055885
§ 371 (c)(1),
(2) Date: Feb. 7, 2017

(87) PCT Pub. No.: WO2016/020828
PCT Pub. Date: Feb. 11, 2016

(65) Prior Publication Data
US 2017/0224645 A1    Aug. 10, 2017

(30) Foreign Application Priority Data
Aug. 8, 2014 (IT) .............. MI2014A1474

(51) Int. Cl.
| *A61K 31/202* | (2006.01) |
| *A61K 9/00* | (2006.01) |
| *A61K 31/164* | (2006.01) |
| *A61K 31/20* | (2006.01) |
| *A61K 9/06* | (2006.01) |

(52) U.S. Cl.
CPC .......... *A61K 31/202* (2013.01); *A61K 9/0014* (2013.01); *A61K 9/0036* (2013.01); *A61K 9/0046* (2013.01); *A61K 9/0048* (2013.01); *A61K 9/06* (2013.01); *A61K 31/164* (2013.01); *A61K 31/20* (2013.01)

(58) Field of Classification Search
None
See application file for complete search history.

(56) References Cited

U.S. PATENT DOCUMENTS 5,679,667 A    10/1997    Francesco

FOREIGN PATENT DOCUMENTS

| DE | 10217131 A1 | 2/2003 |
| EP | 1844784 | 10/2007 |
| WO | 01/24645 A1 | 4/2001 |
| WO | 02/053108 A2 | 7/2002 |
| WO | 2008/075978 | 6/2008 |
| WO | 2014/135529 A1 | 9/2014 |

OTHER PUBLICATIONS

Bergström, S., et al., Biochim Biophys. Acta, vol. 90, p. 204-207, 1964.
International Search Report With Written Opinion for PCT/IB2015/055885 of Oct. 2, 2015.

*Primary Examiner* — Brian J Davis
(74) *Attorney, Agent, or Firm* — Hueschen and Sage

(57) ABSTRACT

The present invention relates to a mixture containing up to two fatty acids selected from palmitic acid, oleic acid, stearic acid, linoleic acid, alpha-linolenic acid, gamma-linolenic acid, eicosapentaenoic acid, docosahexaenoic acid, azelaic acid and myristic acid and palmitoylethanolamide. In one embodiment of the present invention said mixture is characterized in that at least one of said up to two fatty acids is saturated. The present invention also relates to the use of the aforesaid mixture in the treatment of inflammatory and allergic pathologies.

18 Claims, 2 Drawing Sheets

MIXTURE OF FATTY ACIDS AND PALMITOYLETHANOLAMIDE FOR USE IN THE TREATMENT OF INFLAMMATORY AND ALLERGIC PATHOLOGIES

The present invention relates to a mixture containing up to two fatty acids chosen from palmitic acid, oleic acid, stearic acid, linoleic acid, alpha-linolenic acid, gamma-linolenic acid, eicosapentaenoic acid, docosahexaenoic acid, azelaic acid and myristic acid and palmitoylethanolamide.

The present invention also relates to the use of the aforesaid mixture in the treatment of inflammatory and allergic pathologies.

PRIOR ART

Fatty acids are aliphatic carboxylic acids and represent the constituent ingredients of almost all complex lipids and vegetable and animal fats. These compounds can be classified on the basis of the length of the carbon chain and/or on the basis of the presence of double bonds in the aforesaid chain (saturated, unsaturated fatty acids).

In particular, some unsaturated fatty acids are considered to be essential because they are not synthesised by the organism but have to be supplied by the diet. Bergstrom, Samuelsson et al. (Nutrition classics. Biochimica et Biophysica Acta 90:207-10, 1964. The enzymatic formation of prostaglandin E2 from arachidonic acid. Prostaglandins and related factors 32) illustrated in 1964 the role and the biological effects of lipids in the inflammatory process and in other pathologies. In 1979 the first phospholipid, phosphatidylinositol, was discovered as a factor in activating cellular response processes that is able to activate and control reactivity through messaging elements.

Lipids thus have different roles in the organism, including the roles of acting as chemical messengers that can cause changes to the role of the individual cell or determine the actions that are able to modify the microenvironment, as in the case of response processes to inflammatory insults.

Essential fatty acids like linoleic acid and linolenic acid are known for being precursors of the arachidonic acid found in membrane phospholipids (such as, for example, cell membrane) and of many different types of eicosanoids, substances that are involved in the organism's inflammatory response, including hydroxyeicosatetraenes, prostanoids (prostaglandins, thromboxanes and prostacyclins), leukotrienes, lipoxins and resolvins, cell signalling that play an important role in pain, fevers, oedemas, blot clotting and more in general in inflammation.

As is known, inflammatory response is a multifactor physiological reaction characterised by the participation of different cells of the immune system such as, for example, mastocytes, macrophages, basophils and/or lymphocytes having different intervention times.

The first cell to intervene in the inflammatory process is the mastocyte, which is capable of responding to trigger the inflammatory process within microseconds. Activation of the mastocyte generates a series of reactions following the release of preformed mediators contained within the cytoplasm of the mastocyte; in rapid succession, the macrophages are contacted and activated.

The biological systems are based on receptor control: following stimulation of the pathogenic agent, the cells express specific receptors that are saturated by self-produced mediators, i.e. mediators that are formed by fatty acids constituting the membranes of the same cells. The expression of the receptors is the system through which the cells that are involved in the inflammatory process succeed in "transferring" to the microenvironment growth factors, interleukins, cytokines, etc. Saturation of these receptors first enables the degranulation of the mediators inside the cytoplasm of the cells involved in the inflammatory process, which are mainly mastocytes, to be reduced and then modulated until the stimulus induced by the presence of the pathogenic agent is stopped.

However, this regulatory system is exhausted at the moment in which continuing to strip the cellular membranes of fatty acids causes the cell to suffer. In this condition, the receptors remain overexpressed and for the cell this is a degranulation signal of the mediators that trigger defence phenomena that are no longer necessary.

It is thus clear that if the receptor control did not occur, the cells would degranulate everything found in the cytoplasm with the resulting contact of other cells in the microenvironment and this would exasperate the system that by remaining active could become a source of harm and give rise to chronic and autoimmune inflammatory diseases such as, for example, rheumatoid arthritis, multiple sclerosis and systemic lupus erythematosus.

In these pathological conditions, it is thus very important for the organism to be able to control the hyperactivated inflammatory process by forming the receptor antagonist consisting of fatty acids removed from the membrane of the cells.

In order to respond to this need, diet strategies have been devised to reduce the synthesis of pro-inflammatory chemical mediators such as prostaglandins through the diminution of the consumption of vegetable oils and fatty meats and promoting the consumption of fish and certain particular oils such as linseed oil and hemp seed oil. This was done because it was thought that greater quantities of eicosapentaenoic acid and docosahexaenoic acid (omega-3) would be absorbed by the membrane phospholipids in place of arachidonic acid.

It is nevertheless known that these diet strategies are not sufficient to eradicate important inflammatory complaints such as, for example, rheumatoid arthritis, chronic ulcerous colitis, systemic lupus erythematosus, pelvic inflammatory disease or also atherosclerosis and pharmacological treatments must therefore be resorted to.

The pharmacological treatments currently used for inflammatory complaints are corticosteroids (such as for example cortisone or the like) or NSAIDS (nonsteroidal anti-inflammatory drugs), which are drugs that act at different levels of the arachidonic acid cascade.

The function of this cascade is to trigger the immune response, maintaining it until the danger is eliminated and then moderate the immune response until it in turn becomes harmful (as occurs for example in chronic inflammations or in autoimmune diseases). In particular, corticosteroids prevent the cellular processes that lead to the synthesis of proinflammatory and immunostimulant substances and activate those cellular processes that lead to the synthesis of anti-inflammatory immunosuppressive substances so as to reduce the symptoms of the disease.

The side effects of synthetic corticosteroids mostly depend on the fact that in addition to the antiinflammatory/ immunosuppressive effect, they interfere with the organism's homeostatic systems and can thus cause: hypertension, water retention, hyperglycaemia, potassium loss, osteoporosis, muscular hypotrophia, capillary fragility, delayed healing of wounds, hyperlipidaemia, accumulation of adipose tissue in the face, neck and abdomen, gastroduedenal ulcers, increased blood clotting, haematological changes, euphoria and insomnia.

With prolonged treatment, these drugs tend to inhibit the production of similar natural hormones by the adrenal glands, thus causing adrenal insufficiency, which manifests itself with also serious consequences above all when treatment is suspended. Further, the protracted use of corticosteroids is linked to their immunosuppressive action that increases susceptibility to infection.

NSAIDS by contrast interfere at a different level with the arachidonic acid cascade, inhibiting the cyclooxygenase COX1 and 2 involved in the inflammatory processes. Some of the most common side effects affect the gastroenteric apparatus, and in particular the stomach: pain or burning or nausea, ulceration of the gastric mucosa with possible bleeding; skin reactions (rashes, itches) in predisposed subjects.

Palmitoylethanolamide is an endogenous compound belonging to the class of fatty acid starches and is known chemically as N-(2-Hydroxyethyl) hexadecanamide. This compound is a key element in regulating paths connected to the inflammation process, in particular to the process of degranulation downregulation of the mastocyte and also of itch and pain-based processes.

The need is therefore felt to identify one or more compounds for treating the inflammation that is able to block effectively hyperactivation of the inflammatory process, reducing the side effects associated with traditional treatments.

BRIEF DESCRIPTON OF THE DRAWINGS

DESCRIPTON

Figure 1:
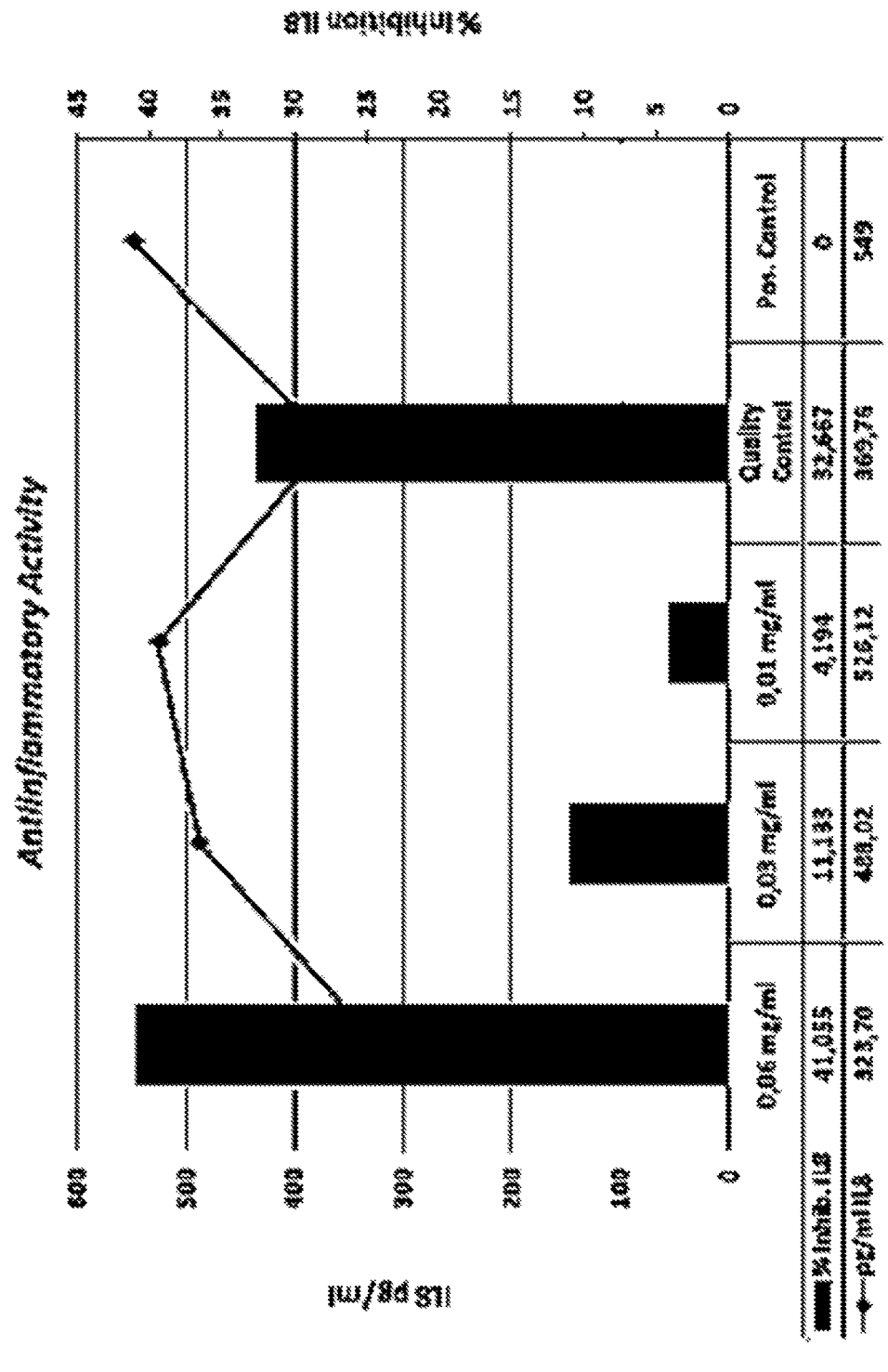
FIG. 1 shows the in vitro antiiflammatory activity of a fatty acid mixture of the present invention, as measured by inhibition of IL-8 release.

It has been surprisingly found that a mixture of specific fatty acids in association with palmitoylethanolamide is able to treat the inflammatory process efficiently, with improved control of the regulatory system and with an absence of side effects through the biological control of the cells involved in the inflammatory process.

One object of the present invention is accordingly a mixture containing up to two fatty acids containing between 8 and 24 carbon atoms; said fatty acids can be saturated, unsaturated or be mixtures thereof, in association with palmitoylethanolamide.

Said fatty acids are preferably selected from palmitic acid, oleic acid, stearic acid, linoleic acid, alpha-linolenic acid, gamma-linolenic acid, eicosapentaenoic acid, docosahexaenoic acid, azelaic acid, myristic acid or a mixture thereof.

According to one embodiment of the present invention, the mixture is characterized in that at least one of said up to two fatty acids is saturated.

Preferably, said saturated fatty acid is selected from stearic acid, palmitic acid, azelaic acid or myristic acid, more preferably, is selected from palmitic acid.

According to a further embodiment of the present invention, the mixture contains a fatty acid selected from the aforesaid fatty acids in association with palmitoylethanolamide.

Preferably, said fatty acid is present in the aforesaid mixture in a weight ratio comprised between 15% and 55%, more preferably between 20% and 53%.

In the aforesaid mixture, the palmitoylethanolamide is contained in a weight quantity comprised between 45% and 85%, preferably between 47% and 80%, of the total weight of the mixture.

Preferably, the aforesaid mixture contains palmitic acid in association with palmitoylethanolamide.

In the mixture of the present invention, the palmitic acid is contained in a weight quantity comprised between 20% and 52%, preferably between 30% and 48%, more preferably about 45%, of the total weight of the mixture.

Preferably, the aforesaid mixture contains the oleic acid in association with palmitoylethanolamide.

In the mixture of the present invention, the oleic acid is contained in a weight quantity comprised between 35% and 48%, preferably between 38% and 45%, more preferably about 40%, of the total weight of the mixture.

Preferably, the aforesaid mixture contains the stearic acid in association with palmitoylethanolamide.

In the mixture of the present invention, the stearic acid is contained in a weight quantity comprised between 30% and 55%, preferably between 38% and 53%, more preferably about 50%, of the total weight of the mixture.

Preferably, the aforesaid mixture contains the linoleic acid in association with palmitoylethanolamide.

In the mixture of the present invention, the linoleic acid is contained in a weight quantity comprised between 35% and 55%, preferably between 40% and 50%, more preferably about 40%, of the total weight of the mixture.

Preferably, the aforesaid mixture contains the alpha-linolenic acid in association with palmitoylethanolamide.

In the mixture of the present invention, the alpha-linolenic acid is contained in a weight quantity comprised between 35% and 48%, preferably between 38% and 42%, more preferably about 40%, of the total weight of the mixture.

Preferably, the aforesaid mixture contains the gamma-linolenic acid in association with palmitoylethanolamide.

In the mixture of the present invention, the gamma-linolenic acid is contained in a weight quantity comprised between 30% and 40%, preferably between 32% and 38%, more preferably about 35%, of the total weight of the mixture.

Preferably, the aforesaid mixture contains the eicosapentaenoic acid in association with palmitoylethanolamide.

In the mixture of the present invention, the eicosapentaenoic acid is contained in a weight quantity comprised between 30% and 55%, preferably between 36% and 52%, more preferably about 50%, of the total weight of the mixture.

Preferably, the aforesaid mixture contains the docosahexaenoic acid in association with palmitoylethanolamide.

In the mixture of the present invention, the docosahexaenoic acid is contained in a weight quantity comprised between 30% and 55%, preferably between 30% and 40%, more preferably about 35%, of the total weight of the mixture.

Preferably, the aforesaid mixture contains the azelaic acid in association with palmitoylethanolamide.

In the mixture of the present invention, the azelaic acid is contained in a weight quantity comprised between 15% and 45%, preferably between 20% and 30%, more preferably about 25%, of the total weight of the mixture.

Preferably, the aforesaid mixture contains the myristic acid in association with palmitoylethanolamide.

In the mixture of the present invention, the myristic acid is contained in a weight quantity comprised between 15% and 35%, preferably between 20% and 30%, more preferably about 25%, of the total weight of the mixture.

According to another particularly preferred embodiment, the mixture contains a fatty acid selected from eicosapentaenoic acid and docosahexaenoic acid in association with palmitoylethanolamide.

According to another embodiment of the present invention, the mixture contains two fatty acids selected from the above fatty acids in association with palmitoylethanolamide.

Preferably, the two fatty acids are present in the aforesaid mixture in a weight ratio to one another comprised between 0.25 and 2.33, more preferably between 0.33 and 1.5, still more preferably about 1.

Furthermore, in the aforesaid mixture the two fatty acids are present in a weight ratio to the palmitoylethanolamide comprised between 0.25 and 1.5, preferably between 0.43 and 1, more preferably about 0.67.

When two fatty acids are present in the mixture of the present invention, the palmitoylethanolamide is present in a weight quantity comprised between 25% and 70%, preferably between 35% and 60%, of the total weight of the mixture.

The two fatty acids are present in the mixture of the invention in a weight quantity comprised between 30% and 75%, preferably between 40% and 65%, of the total weight of the mixture.

According to one embodiment, the mixture of the invention contains palmitic acid, preferably in a weight quantity comprised between 10% and 48%, more preferably between 25% and 35%, still more preferably about 30%, of the total weight of the mixture.

Alternatively, the mixture of the invention can contain oleic acid, preferably in a weight quantity comprised between 15% and 38%, more preferably between 18% and 25%, still more preferably about 20%, of the total weight of the mixture.

According to another embodiment of the invention, the aforesaid mixture can contain stearic acid, preferably in a weight quantity comprised between 20% and 45%, more preferably comprised between 25% and 35%, still more preferably about 30%, of the total weight of the mixture.

Otherwise, the linoleic acid can be contained in the mixture of the present invention, preferably in a weight quantity comprised between 15% and 40%, more preferably between 20% and 38%, still more preferably about 35%, of the total weight of the mixture.

According to another embodiment of the present invention, the mixture contains the alpha-linolenic acid, preferably in a weight quantity comprised between 25% and 38%, more preferably comprised between 30% and 36%, still more preferably about 35%, of the total weight of the mixture.

According to the present invention, the mixture can contain gamma-linolenic acid, preferably in a weight quantity comprised between 15% and 35%, more preferably between 20% and 34%, still more preferably about 30%, of the total weight of the mixture.

According to another embodiment of the invention, the aforesaid mixture can contain eicosapentaenoic acid, preferably in a weight quantity comprised between 10% and 35%, more preferably comprised between 20% and 30%, still more preferably about 25%, of the total weight of the mixture.

Alternatively, the docosahexaenoic acid can be contained in the mixture, preferably in a weight quantity comprised between 8% and 35%, more preferably between 18% and 30%, still more preferably about 20%, of the total weight of the mixture.

According to the present invention, the aforesaid mixture can contain azelaic acid, preferably in a weight quantity comprised between 5% and 35%, more preferably between 10% and 20%, still more preferably about 15%, of the total weight of the mixture.

According to another embodiment of the present invention, the mixture contains the myristic acid, preferably in a weight quantity comprised between 15% and 30%, more preferably comprised between 15% and 20%, still more preferably about 18%, of the total weight of the mixture.

According to another particularly preferred embodiment, the mixture of the invention contains two fatty acids selected from eicosapentaenoic acid and docosahexaenoic acid in association with palmitoylethanolamide.

In the aforesaid mixture, the eicosapentaenoic acid is present in a weight quantity comprised between 20% and 40%, preferably about 30%.

The docosahexaenoic acid is present in a quantity comprised between 25% and 50%, preferably about 30%.

Palmitoylethanolamide is present in the aforesaid preferred mixture in a quantity comprised between 30% and 50%, preferably about 40%.

It has been surprisingly noticed that by making up a pool of the aforesaid fatty acids, in particular one or two fatty acids according to the present invention, it is possible to determine the control of cells involved in the inflammatory processes such as mastocyctes, macrophages, basophils and lymphocytes.

This system for administering the fatty acids with palmitoylethanolamide has two important advantages:

1) a more rapid and reactive response to the hyperstimulation induced by the inflammatory agent: the cell does not have to be deprived of the membrane lipids with consequent temporal "dispersal";

2) significant energy saving: the cell does not have to use energy to recover the lipids from the membranes and to replace the lipids.

It has in fact been observed that by supplying the pool of fatty acids according to the present invention, improved control of the inflammatory process is obtained as well as rapid restoration of physiological conditions and of normal conditions of the microenvironment affected compared with what is known in the prior art.

A further object of the present invention is a pharmaceutical composition comprising the aforesaid mixture and at least one pharmaceutically acceptable excipient.

The term "pharmaceutically acceptable excipient" refers to a substance that is devoid of any pharmacological effect of its own and does not produce adverse reactions when administered to a mammal, preferably to a human being. Pharmaceutically acceptable excipients are well known in the prior art and are disclosed, for example in the *Handbook of Pharmaceutical Excipients, sixth edition* 2009, which is included here for reference.

Excipients are normally classified according to the function that they have in the final pharmaceutical composition. Preferably, suitable excipients according to the present invention are for example diluent, adsorbent, glidant, binder, lubricant, surfactant, disintegrating, preservatives, antioxidant or mixtures thereof.

According to one embodiment of the present invention, the aforesaid composition comprises a mixture containing up to two fatty acids, or containing one or two fatty acids, selected from palmitic acid, oleic acid, stearic acid, linoleic acid, alpha-linolenic acid, gamma-linolenic acid, eicosapentaenoic acid, docosahexaenoic acid, azelaic acid, myristic acid, palmitoylethanolamide and at least one pharmaceutically acceptable excipient.

When the palmitic acid is contained in the composition of the invention it is present in a quantity in weight comprised between 10% and 48%, more preferably comprised between 20% and 30%, still more preferably about 25%.

When the oleic acid is contained in the composition of the invention it is present in a quantity in weight comprised between 15% and 38%, more preferably comprised between 15% and 25%, still more preferably about 20%.

When the stearic acid is contained in the composition of the invention it is present in a quantity in weight comprised between 20% and 45%, more preferably comprised between 25% and 35%, still more preferably about 30%.

When the linoleic acid is contained in the composition of the invention it is present in a quantity in weight comprised between 15% and 40%, more preferably comprised between 25% and 35%, still more preferably about 30%.

When the alpha-linolenic acid is contained in the composition of the invention, it is present in a quantity in weight comprised between 25% and 38%, more preferably comprised between 28% and 32%, still more preferably about 30%.

When the gamma-linolenic acid is contained in the composition of the invention, it is present in a quantity in weight comprised between 15% and 30%, more preferably comprised between 20% and 30%, still more preferably about 25%.

When the eicosapentaenoic acid is contained in the composition of the invention it is present in a quantity in weight comprised between 10% and 35%, more preferably comprised between 15% and 25%, still more preferably about 20%.

When the docosahexaenoic acid is contained in the composition of the invention, it is present in a weight quantity comprised between 8% and 35%, more preferably comprised between 15% and 25%, still more preferably about 20%.

When the azelaic acid is contained in the composition of the invention it is present in a quantity in weight comprised between 5% and 35%, more preferably comprised between 10% and 20%, still more preferably about 15%.

When the myristic acid is contained in the composition of the invention it is present in a quantity in weight comprised between 15% and 30%, more preferably comprised between 15% and 25%, still more preferably about 20%.

The composition of the invention further contains a quantity of palmitoylethanolamide comprised between 35% and 55%, preferably comprised between 35% and 45%, more preferably about 40%.

The aforesaid percentage quantities are weight quantities expressed as a percentage the total weight of the composition.

The composition of the present invention can be formulated in a form that is suitable for oral, topical, rectal, vaginal, ophthalmic or parenteral administration.

According to one preferred embodiment of the present invention, said oral form is selected from a tablet, capsule, granule, oily pearl, solution, suspension, aerosol, more preferably is selected from a capsule or tablet.

The capsule can be a soft gelatine capsule, a hard capsule or a capsule containing granules.

According to another preferred embodiment of the present invention, said topical form is selected from cream, ointment, gel, salve, solution, suspension, eyewash, drops, spray, or powder, more preferably it is selected from cream, gel, spray, ointment, drops, eyewash.

According to another preferred embodiment of the present invention, said form that is suitable for vaginal administration is a pessary, cannula, douche or cream.

According to another preferred embodiment of the present invention, said form that is suitable for rectal administration is a suppository, an enema or a cream.

According to another preferred embodiment of the present invention, said form that is suitable for ophthalmic administration is an eyewash, a bath or a cream.

According to another preferred embodiment of the present invention, said form that is suitable for parenteral administration is selected from a water buffer solution or oily suspension.

The mixture of fatty acids of the present invention is preferably contained in the aforesaid formulations in a weight quantity that varies from 3% to 60%, preferably from 5% to 35%, of the total weight of the formulation.

According to one embodiment of the present invention, the composition containing a mixture of a fatty acid and palmitoylethanolamide is preferably formulated in topical form.

According to one embodiment of the present invention, the composition containing a mixture of one or two fatty acids and palmitoylethanolamide is preferably formulated in topical or oral form.

According to one embodiment of the present invention, the composition containing a mixture of two fatty acids and palmitoylethanolamide is preferably formulated in oral form, more preferably in the form of a tablet, of a suspension, in rectal form or in topical form, more preferably in the form of a cream, gel, ointment, drops, eyewash, spray, solution.

According to the invention, the composition of the present invention can be administered to animals and humans, defined as adults and as "paediatric population", wherein with the term "pediatric polulation " is indicated the part of the population from birth to eighteen years of age.

A further object of the present invention is to use a mixture containing up to two fatty acids selected from palmitic acid, oleic acid, stearic acid, linoleic acid, alpha-linolenic acid, gamma-linolenic acid, eicosapentaenoic acid (EPA), docosahexaenoic acid (DHA), azelaic acid, myristic acid and palmitoylethanolamide and/or a composition containing said mixture in the treatment of inflammatory and allergic pathologies.

Said inflammatory and allergic pathologies are acute or chronic and are selected from dermatological pathologies such as, for example, atopical dermatitis, dermatomyositis scleroderma, psoriasis, polymyositis, pemphigus, pemphigoidepidermolysis bullosa; ophthalmic pathologies such as, for example, Sjorgen's syndrome, sympathetic ophthalmia, uveitis, uveoretinitis; mucosal pathologies such as inflammation of the gastrointestinal mucous membranes (Crohn's disease), inflammation of the oral and genital mucous membrane; joint and connective tissue pathologies such as, for example, rheumatoid arthritis, psoriatic arthritis, arthritis from lupus erythematosus, discoid and systemic lupus; chronic pathological inflammations such as for example from chronic solar dermatitis, asthma and intestinal and pulmonary fibrosis, chronic arthritis, degenerative pathologies of the peripheral nervous system (PNS) and of the central nervous system (CNS) such as, for example, multiple sclerosis, neurodegenerative pathologies, not only autoimmune inflammatory processes connected to CNS like Parkinson's disease, tinnitus, senile dementia, bacterial meningitis, HIV infections and trauma injuries, and PNS pathologies such as, for example, radiculopathy of inflammatory origin; pathologies of the peripheral and central system where the inflammatory processes follow the first insult of ischaemic origin, such as, for example, compression and traumatic neuropathies, cerebral strokes and traumatic brain injury; heart disease arising from perfusion phenomena as a consequence of ischaemic damage; inflammatory pathologies associated with fibrosis, such as, for example, allergic conjunctivitis, giant papillary conjunctivitis, dietary allergies, scarring anomalies such as, for example, hypertrophic scars, keloids and cicatricial pemphigoid; pathologies in which renal function is altered following renal inflammation.

Preferred pathologies according to the present invention are the inflammatory pathologies linked to hyperactivity of the cells involved in the inflammatory processes on a neurogenic basis, more preferably they are neuroinflammatory pathologies of the central and peripheral nervous system, such as, for example, tinnitus, polyneuropathies, myasthenia, myopathies.

The composition of the present invention is preferably administered daily, from one to four doses a day, in which said dose contains from 0.1 to 50 mg of composition/kg of body weight of patient, more preferably from 0.5 to 20 mg/kg of body weight of patient, for at least 4 weeks.

EXAMPLES

The following mixtures according to the present invention were prepared.

Example 1

Formulation in Topical Cream

| | |
|---|---|
| Eicosapentaenoic acid | 40% |
| Palmitoylethanolamide | 60% |

Example 2

Formulation in Vaginal Pessary

| | |
|---|---|
| Docosahexaenoic acid | 45% |
| Palmitoylethanolamide | 55% |

Example 3

Formulation in Otological Drops

| | |
|---|---|
| Eicosapentaenoic acid | 30% |
| Docosahexaenoic acid | 30% |
| Palmitoylethanolamide | 40% |

Example 4

Formulation in Cream for Periophthalmic Use

| | |
|---|---|
| Eicosapentaenoic acid | 35% |
| Docosahexaenoic acid | 30% |
| Palmitoylethanolamide | 35% |

Example 5

Evaluation of the Anti-inflammatory Activity In Vitro

A mixture of fatty acids containing: palmitoylethanolamide (33%), linoleic acid (33%) and palmitic acid (33%) (defined in the tables as Fatty Acids) was tested in vitro on a human cell line THP1 (monocyte-macrophage) previously sensitized with LPS (1 µg/ml), a known inflammatory agent, to evaluate the activity of the mixture to reduce the release of pro-inflammatory mediators (IL-6 and IL-8).

Results

Figure 2:
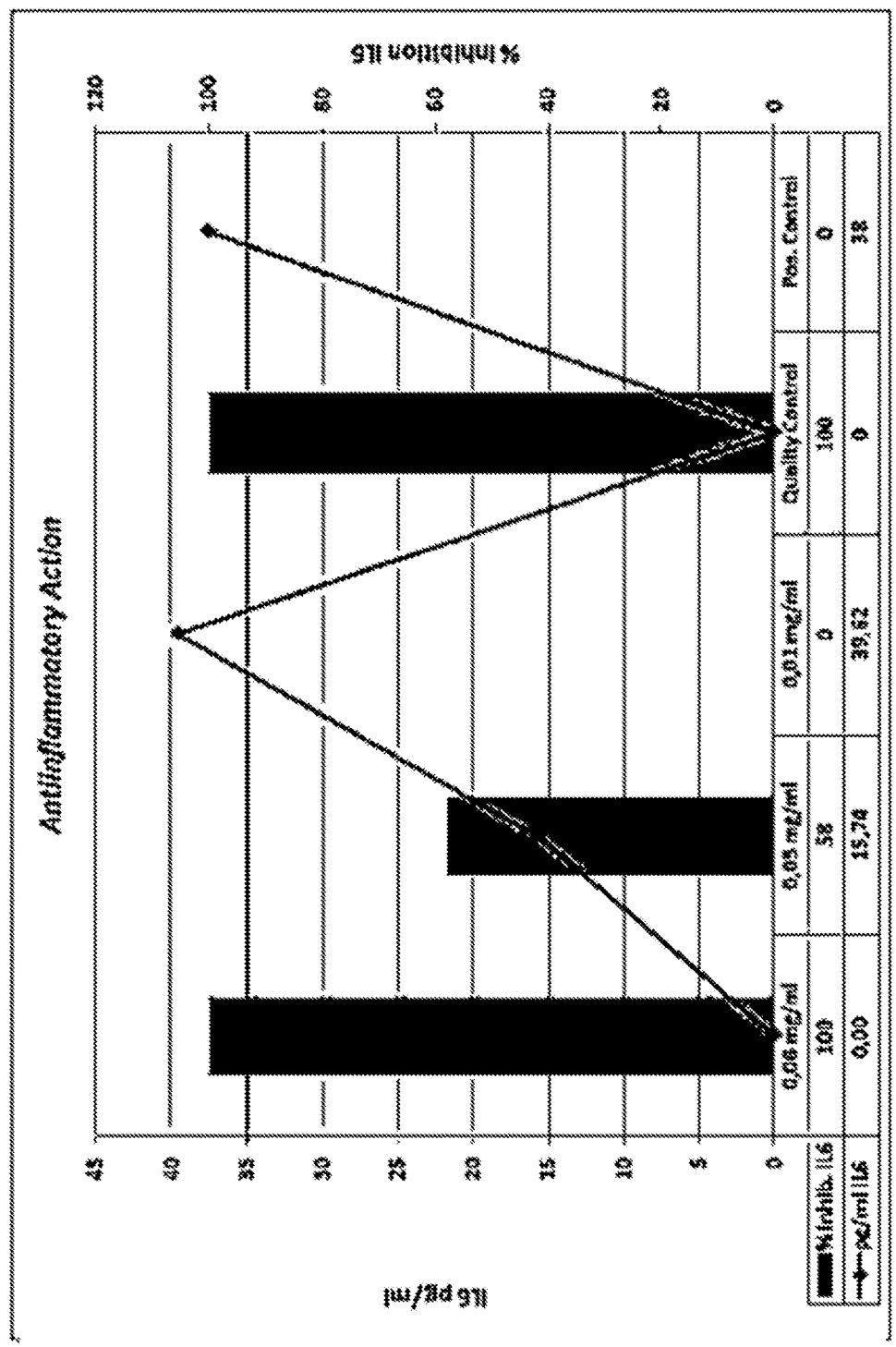
FIG. 2 shows the in vitro antiiflamrnatory activity of a fatty acid mixture of the present invention, as measured by inhibition of IL-6 release.

All doses of the mixture analyzed have proved to be able to inhibit the release of both cytokines checked IL-6 and IL-8 (FIGS. 1 and 2, Table 1 and 2). The tests performed have identified two effective doses 0.06 mg/ml and 0.03 mg/ml: at these concentrations in fact the anti-inflammatory effectiveness of fatty acids mixture determines a strong reduction of IL-6 release equal to 100% and 58% respectively, and at 0.06 mg/ml it causes a IL-8 release inhibition equal to 42.7%.

TABLE 1

| Acidi Grassi + LPS | pg/ml IL8 | % Inhib. IL8 |
|---|---|---|
| 0.06 mg/ml | 323.70 | 41.06 |
| 0.03 mg/ml | 488.02 | 11.13 |
| 0.01 mg/ml | 526.12 | 4.19 |
| Quality Control | 369.76 | 32.67 |
| Pos. Control | 549 | 0 |

TABLE 2

| Acidi Grassi + LPS | g/ml IL6 | % Inhib. IL6 |
|---|---|---|
| 0.06 mg/ml | 0 | 100 |
| 0.03 mg/ml | 15.74 | 58 |
| 0.01 mg/ml | 39.62 | 0 |
| Quality Control | 0 | 100 |
| Pos. Control | 38 | 0 |

The invention claimed is:

1. A mixture comprising two fatty acids selected from palmitic acid, oleic acid, stearic acid, linoleic acid, alpha-linolenic acid, gamma-linolenic acid, eicosapentaenoic acid (EPA), docosahexaenoic acid (DHA), azelaic acid and myristic acid and palmitoylethanolamide.

2. The mixture according to claim 1, wherein at least one of the two fatty acids is saturated.

3. The mixture according to claim 1, wherein the two fatty acids are present in the mixture in a weight ratio from one to another comprised between 0.25 and 2.33.

4. The mixture according to claim 1, wherein the two fatty acids are present in a weight ratio with respect to the palmitoylethanolamide comprised between 0.25 and 1.5.

5. The mixture according to claim 1, wherein the palmitoylethanolamide is present in the mixture in a weight quantity comprised between 25% and 70% of the total weight of the mixture.

6. The mixture according to claim 1, wherein the two fatty acids are present in the mixture in a weight quantity comprised between 30% and 75% of the total weight of the mixture.

7. A composition comprising the mixture according to claim 1 and at least one pharmaceutically acceptable excipient.

8. The composition according to claim 7, formulated in an oral, topical, rectal, vaginal, ophthalmic or parenteral form.

9. The composition according to claim 8, which is an oral form selected from a tablet, capsule, granule, oily pearl, solution, suspension and aerosol.

10. The composition according to claim 8, which is a topical form selected from cream, ointment, gel, salve, solution, suspension, eyewash, spray, drops and powder.

11. The composition according to claim 8, which is a parenteral form selected from a water buffer solution and oily suspension.

12. The composition according to claim 8, which is a rectal form selected from a suppository, a cream and an enema.

13. The composition according to claim 8, which is a vaginal form selected from a pessary, a cream and a vaginal douche.

14. The composition according to claim 8, which is an ophthalmic form selected from an eyewash, a cream and a bath.

15. The composition according to claim 7, wherein the mixture is present in the composition in a weight quantity comprised between 15% and 70% of the total weight of the composition.

16. A method of treating a condition selected froth inflammatory and allergic pathologies in a subject in need thereof, comprising administering an effective amount of the mixture according to claim 1, alone or in combination with one or more pharmaceutically acceptable excipients.

17. The method according to claim 16, wherein the mixture is administered daily, from one to four doses a day, wherein the dose contains from 0.1 to 50 mg of composition/kg of patient body weight, for at least 4 weeks.

18. A composition comprising the mixture according to claim 1, wherein the composition is appropriately packaged for once-a-day administration of the mixture, from one to four doses a day, wherein the dose contains from 0.1 to 50 mg of composition/kg of patient body weight, for at least 4 weeks.

* * * * *

UNITED STATES PATENT AND TRADEMARK OFFICE
CERTIFICATE OF CORRECTION

PATENT NO. : 9,962,355 B2
APPLICATION NO. : 15/502316
DATED : May 8, 2018
INVENTOR(S) : Raffaele Migliaccio, Antonella Sardei and Carmela Migliaccio It is certified that error appears in the above-identified patent and that said Letters Patent is hereby corrected as shown below:

On the Title Page

Column 1, item (30): "MI2014A1474" should read -- MI2014A1474 --.

In the Claims

Column 12, Line 11: "froth" should read -- from --.

Signed and Sealed this
Twenty-sixth Day of June, 2018

Andrei Iancu
*Director of the United States Patent and Trademark Office*

UNITED STATES PATENT AND TRADEMARK OFFICE
CERTIFICATE OF CORRECTION

PATENT NO. : 9,962,355 B2  
APPLICATION NO. : 15/502316  
DATED : May 8, 2018  
INVENTOR(S) : Raffaele Migliaccio, Antonella Sardei and Carmela Migliaccio Page 1 of 1

It is certified that error appears in the above-identified patent and that said Letters Patent is hereby corrected as shown below:

On the Title Page

Column 1, item (30): "MI2014A1474" should read -- MI2014A001474 --.

In the Claims

Column 12, Line 11: "froth" should read -- from --.

This certificate supersedes the Certificate of Correction issued June 26, 2018.

Signed and Sealed this  
Thirteenth Day of August, 2019

Andrei Iancu  
*Director of the United States Patent and Trademark Office*